United States Patent [19]

Montgomery

[11] Patent Number: 4,652,408

[45] Date of Patent: Mar. 24, 1987

[54] INHALATION APPARATUS

[75] Inventor: Frederick J. Montgomery, Keighley, United Kingdom

[73] Assignee: The BOC Group plc, Windlesham, United Kingdom

[21] Appl. No.: 846,438

[22] Filed: Mar. 31, 1986

[30] Foreign Application Priority Data

Apr. 4, 1985 [GB] United Kingdom ................ 8508922

[51] Int. Cl.⁴ ............................................ A61M 15/00
[52] U.S. Cl. ................................ 261/130; 128/203.17;
128/203.27; 128/204.13; 219/274; 219/275;
219/331; 261/142; 261/104
[58] Field of Search ............... 261/130, 131, 142, 104;
128/203.17, 203.27, 204.13; 219/274, 275, 271,
272, 331

[56] References Cited

U.S. PATENT DOCUMENTS

| | | | |
|---|---|---|---|
| 3,695,267 | 10/1972 | Hirtz et al. | 128/203.17 |
| 3,982,095 | 9/1976 | Robinson | 128/204.13 |
| 4,036,915 | 7/1977 | Lucero et al. | 261/142 |
| 4,038,980 | 8/1977 | Fodor | 261/130 |
| 4,101,611 | 7/1978 | Williams | 128/203.17 |
| 4,225,542 | 9/1980 | Wall et al. | 261/131 |
| 4,484,576 | 11/1984 | Albarda | 128/203.27 |

FOREIGN PATENT DOCUMENTS

| | | | |
|---|---|---|---|
| 1364127 | 8/1974 | United Kingdom | 128/203.27 |
| 1448473 | 9/1976 | United Kingdom | |

Primary Examiner—Tim Miles
Attorney, Agent, or Firm—Roger M. Rathbun; Larry R. Cassett

[57] ABSTRACT

A humidifier includes a chamber 14 having an inlet 30 and an outlet 6. The chamber 14 is releasably attached to a heater unit including a heater 22 and a heat sensor 24. When the chamber 14 and the heater unit are assembled together the heater 22 is in thermal contact with a heat transfer surface of the chamber 14 at or adjacent the inlet port 30 while the temperature sensor 24 is in thermal contact with the heat transfer surface at or adjacent the outlet port 6.

5 Claims, 3 Drawing Figures

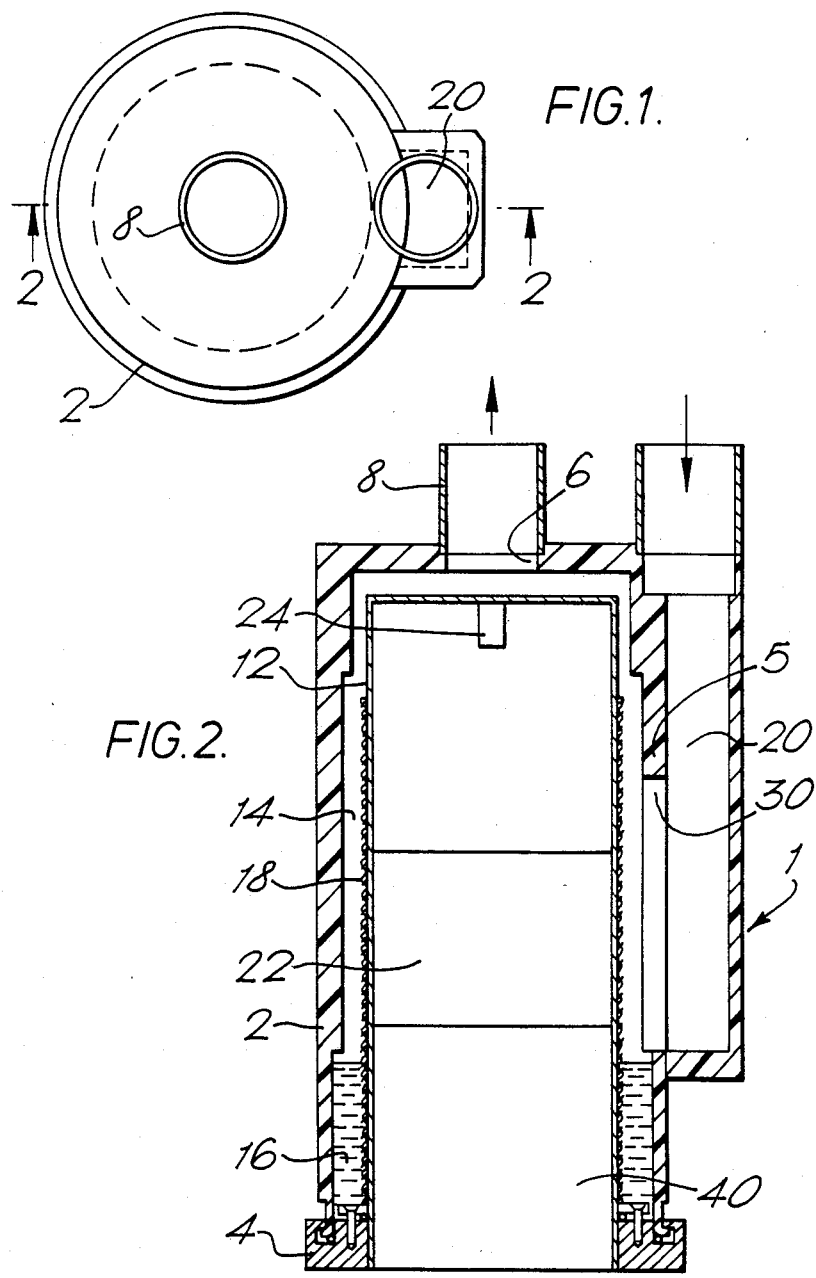

INHALATION APPARATUS

BACKGROUND OF THE INVENTION

The present invention relates to inhalation apparatus and in particular to medical humidifiers.

Medical humidifiers are used with intensive care ventilators to heat and humidify dry medical gases to specified levels before said gases are inhaled by a patient.

A medical humidifier is known from UK patent No. 1448473 which includes a reservoir for water in communication with a humidification chamber. The humidification chamber has an inlet for gas to be humidified and an outlet for warm humidified gas. Heat is transferred to the humidification chamber by a heating coil. A delivery line extends between the outlet port of the humidification chamber and a delivery point.

In a modification of this known medical humidifier, a control system including a temperature sensor controls the heater power to the humidifying chamber to maintain the outlet gas temperature at a set value despite changes in gas flowrate through the humidification chamber. The design of the chamber ensures the outlet gas is fully saturated with water vapour by including a large water evaporating surface using wick materials.

However, there is a problem associated with this known type of humidifier in that the temperature sensor is thermally isolated from the heater and relies on gas flow to indicate the gas temperature in the humidification chamber. If there is a period in which no gas flows, then the temperature of the gas at the sensor starts to fall and the control system responds to this fall by increasing the power to the heater and this results in a system heading towards its maximum operating temperature. When the gas flow is turned on again, a transient temperature overshoot occurs.

SUMMARY OF THE INVENTION

It is an aim of the present invention to provide a humidifier designed to enable accurate control of the outlet gas temperature and humidity and ensure the system is controlled to a safe operating temperature during a period of no gas flow.

According to the present invention, an apparatus for delivering humidified gas to a patient comprises a humidification chamber at least a portion of which is a heat transfer surface, the chamber having an inlet port for gas to be humidified and an outlet port spaced therefrom for the humidified gas, the humidification chamber being releasably attached to a heater unit comprising a heater, and a temperature sensor thermally isolated therefrom and so arranged that when the humidification chamber and the heater unit are assembled together, the heater is in thermal contact with the heat transfer surface at or adjacent the inlet port and the temperature sensor is in contact with the heat transfer surface at or adjacent the outlet port.

BRIEF DESCRIPTION OF DRAWINGS

An embodiment of the invention will now be described, by way of example, reference being made to the Figures of the accompanying diagrammatic drawings, in which:

FIG. 1 is a plan view of a medical humidifier;

FIG. 2 is a transverse cross-section on line 2—2 of FIG. 1; and

DESCRIPTION OF PREFERRED EMBODIMENT

Figure 3:
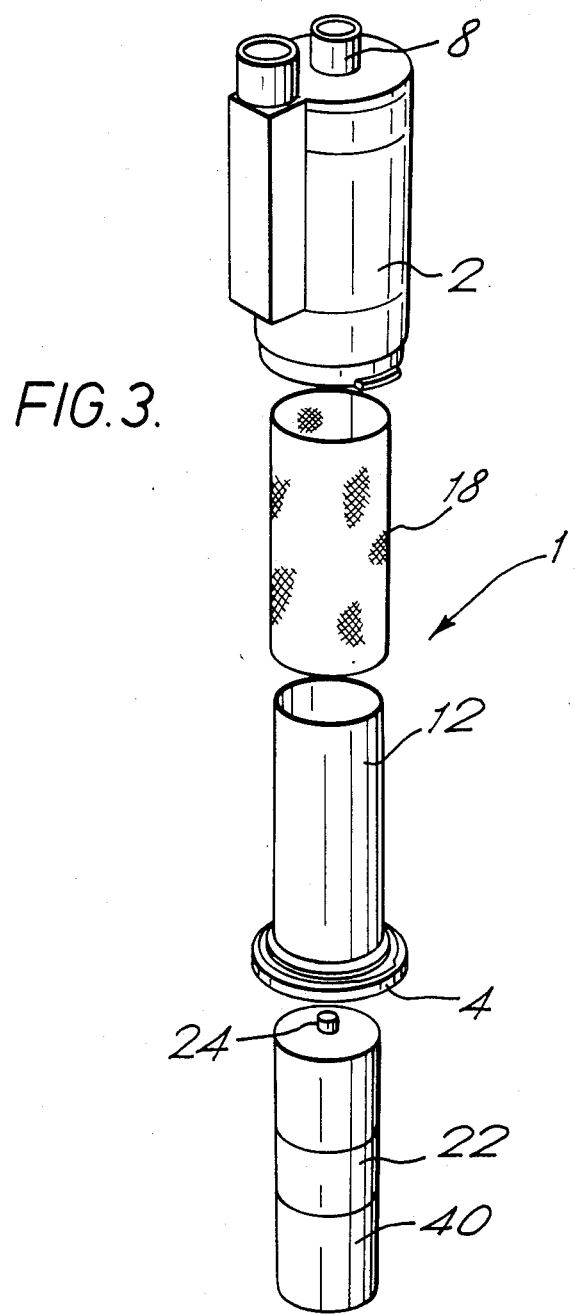
FIG. 3 is an exploded perspective view of the medical humidifier of FIGS. 1 and 2.

As shown in the Figures, an apparatus 1 for delivering humidified gas to a patient comprises an outer housing 2 of plastics material having thermally insulating properties. At one (lower as shown) end the housing 2 is attached to a closure plate 4 and at its opposite (upper as shown) end is an outlet port 6 communicating with an outlet spigot 8. The housing 2 has a substantially inverted cup shape. Moulded to the housing 2 is an inlet chamber 20. The common wall 5 of the inverted cup shape housing 2 and the inlet chamber 20 has an inlet port 30.

Arranged coaxially within the housing 2 is an inverted cup-shaped metallic member 12 having good heat conducting properties. The member 12 which may be made of aluminum is spaced from the housing 2 so that between them the housing 2 and the member 12 define an annular humidification chamber 14.

At its lower end (as shown) the member 12 is attached to the closure plate 4. The housing 2 is counterbored at its lower end so that the space between the inner surface of the housing 2 and the outer surface of the member 12 is greater adjacent the closure plate 4 than elsewhere and this enlarged space defines a reservoir 16 for water.

Along the outside of the member 12 is a wick 18 which extends substantially along the length of the humidification chamber 14 and into the reserovir 16.

In use, the assembly of the housing 2, member 12, wick 18 and closure plate 4 fits over, in a releasably detachable manner, a heater unit 40 in the form of a cylindrical column which includes a heater 22, a spring loaded temperature sensor 24 and a power control circuit (not shown). The arrangement is such that the location of the heater 22 is approximately half way up the member 12 and adjacent the inlet 30; and the location of the temperature sensor 24 is at the upper end of the member 12 and adjacent the outlet 6. Both the heater 22 and the sensor 24 are in thermal contact with the member 12 but are thermally isolated one from the other except through the member 12. As will be explained, the power control circuit known per se controls the power to the heater 22 according to signals received from the sensor 24.

In operation, gas for delivery to the patient enters the inlet chamber 20 and passes through inlet 30 and into the humidification chamber 14. The control circuit controls the power to the heater 22 to maintain a constant set temperature at the sensor 24. As water is evaporated along the whole length of the humidification chamber 14, the unheated part of the heat transfer surface of the member 12 cools and approaches the temperature of the gas passing through the outlet 6. Hence by controlling the temperature sensor 24 to a set level, the outlet gas temperature is indirectly controlled to a similar level.

During a period of no gas flow, there is no cooling along the heat transfer surface and the temperature at the temperature sensor 24 will rise. The power control circuit will then reduce the power to the heater 22 to ensure the temperature remains at the set level and hence ensures no high temperature overshoot when the gas is flowing once again.

I claim:

1. An apparatus for delivering humidified gas to a patient comprising a humidification chamber at least a portion of which is a heat transfer surface, the chamber having an inlet port for gas to be humidified and an outlet port spaced therefrom for the humidified gas, the humidification chamber being releasably attached to a heater unit comprising a heater and a temperature sensor thermally isolated therefrom and so arranged that when the humidification chamber and the heater unit are assembled together, the heater is in thermal contact with the heat transfer surface at or adjacent the inlet port and the temperature sensor is in thermal contact with the heat transfer surface at or adjacent the outlet port.

2. An apparatus as claimed in claim 1, in which the humidification chamber is defined by a portion of the space between an inner metallic member having good heat conducting properties and an outer housing having good thermally insulating properties, the remainder of said space defining a reservoir for water.

3. An apparatus as claimed in claim 2, in which a wick is arranged in said space and extends from the humidification chamber into the reservoir.

4. An apparatus as claimed in claim 2, in which the heater unit is in the form of a cylindrical column and the inner metallic member has an inverted cup-shaped configuration which receives the cylindrical column.

5. An apparatus for delivering humidified gas to a patient comprising an inner metallic member having good heat conducting properties and an outer housing having good thermally insulating properties spaced from the inner metallic member, at least a portion of the said space between the inner metallic member and the outer housing defining a humidification chamber whilst the remainder of said space defines a reservoir for water, the humidification chamber having an inlet port for gas to be humidified and an outlet port spaced from the inlet port for the humidified gas, and a heater unit in the form of a cylindrical column including a heater and a temperature sensor thermally isolated from the heater, the heater being in thermal contact with the inner metallic member at or adjacent the inlet port and the temperature sensor being in thermal contact with the inner metallic member at or adjacent the outlet port.

* * * * *